United States Patent
Thomas et al.

(10) Patent No.: US 11,166,991 B2
(45) Date of Patent: Nov. 9, 2021

(54) BACTERIAL STRAIN AS AGENTS FOR PREVENTING AND/OR TREATING RESPIRATORY DISORDERS

(71) Applicant: Institut National De La Recherche Agronomique, Paris (FR)

(72) Inventors: Muriel Thomas, Igny (FR); Aude Remot-Brizion, Semblancay (FR); Philippe Langella, Vélizy (FR)

(73) Assignee: Institut National De La Recherche Agronomique, Paris (FR)

( * ) Notice: Subject to any disclaimer, the term of this patent is extended or adjusted under 35 U.S.C. 154(b) by 143 days.

(21) Appl. No.: 16/072,672

(22) PCT Filed: Jan. 27, 2017

(86) PCT No.: PCT/EP2017/051839
§ 371 (c)(1),
(2) Date: Jul. 25, 2018

(87) PCT Pub. No.: WO2017/129787
PCT Pub. Date: Aug. 3, 2017

(65) Prior Publication Data
US 2019/0030094 A1    Jan. 31, 2019

(30) Foreign Application Priority Data

Jan. 27, 2016 (FR) ...................... 1650656

(51) Int. Cl.
| | |
|---|---|
| *A61K 35/744* | (2015.01) |
| *A61P 11/00* | (2006.01) |
| *C12N 1/20* | (2006.01) |
| *A61K 35/00* | (2006.01) |
| *C12R 1/46* | (2006.01) |

(52) U.S. Cl.
CPC ............ *A61K 35/744* (2013.01); *A61P 11/00* (2018.01); *C12N 1/20* (2013.01); *C12N 1/205* (2021.05); *A61K 2035/11* (2013.01); *C12R 2001/46* (2021.05)

(58) Field of Classification Search
CPC .......... A61K 35/744; C12N 1/20; A61P 11/00
See application file for complete search history.

(56) References Cited

U.S. PATENT DOCUMENTS

2008/0096266 A1* 4/2008 Komeda .................... A23L 2/52
435/252.9

FOREIGN PATENT DOCUMENTS

RU    2575562 C1 *  2/2016

OTHER PUBLICATIONS

T. Shimada et al., Lysed Enterococcus faecalis FK-23 oral administration reveals inverse association between tuberculin responses and clinical manifestations in perennial allergic rhinitis: a pilot study, 2004, J Invest Allergol Clin Immunol, vol. 14(3), pp. 187-192. (Year: 2004).*

(Continued)

*Primary Examiner* — David W Berke-Schlessel
*Assistant Examiner* — Trent R Clarke
(74) *Attorney, Agent, or Firm* — Knobbe, Martens, Olson and Bear, LLP

(57) ABSTRACT

The invention relates to a novel bacterial strain deposited with the CNCM under number 1-4969. This strain has properties that are useful in the treatment of respiratory disorders. The invention also relates to compositions and uses of said strain.

23 Claims, 17 Drawing Sheets

(56) References Cited

OTHER PUBLICATIONS

Figure 1:
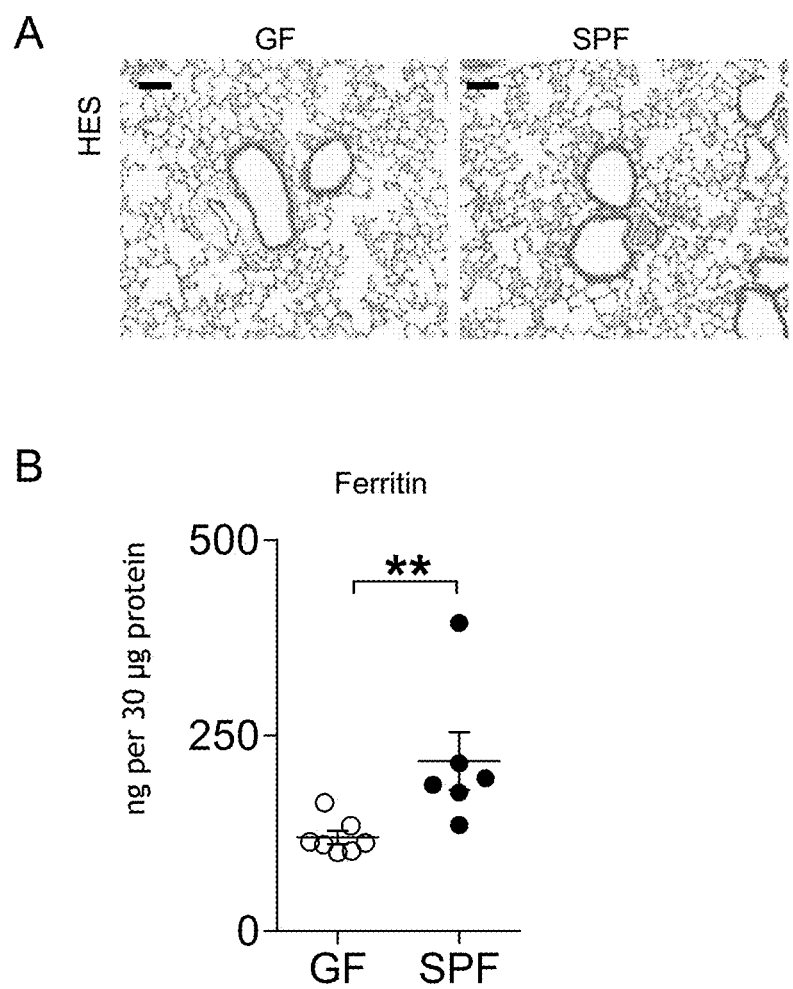
Figure 1:
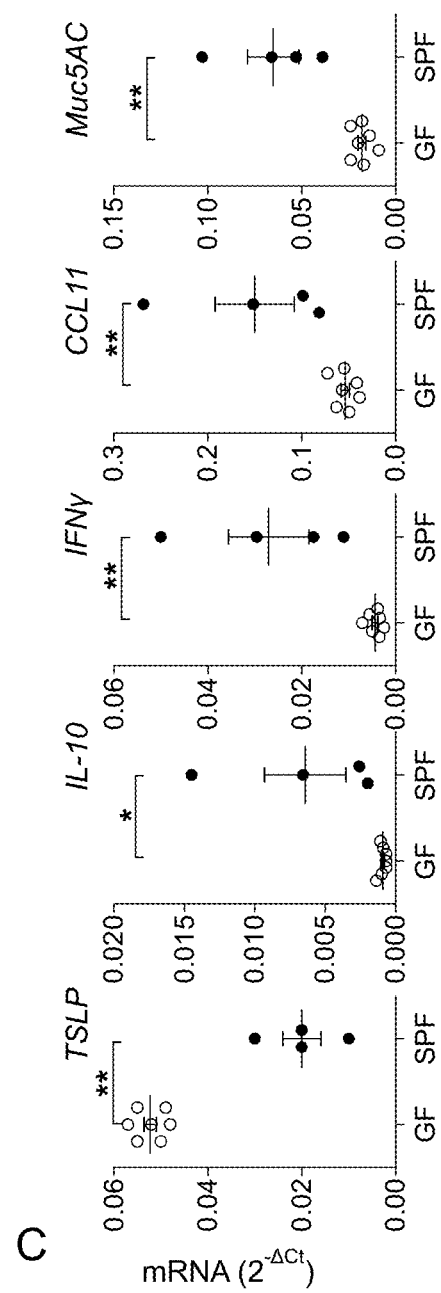
Figure 1:
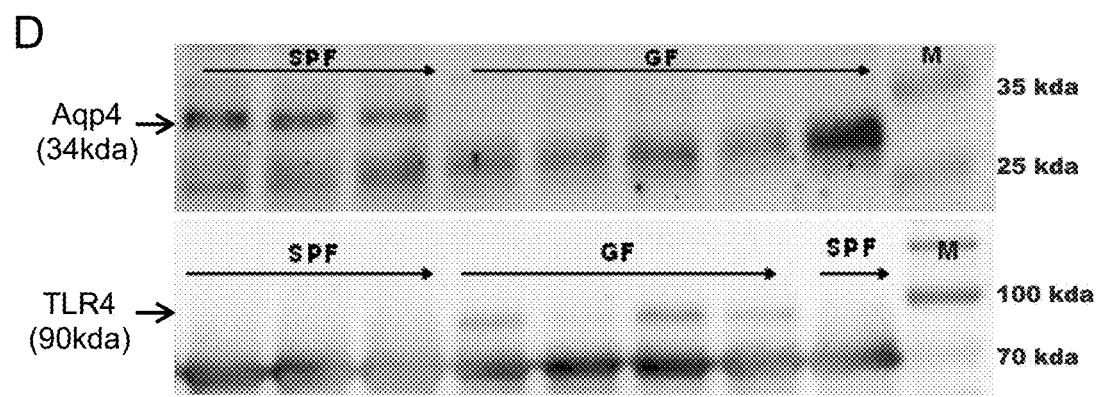
Figure 1:
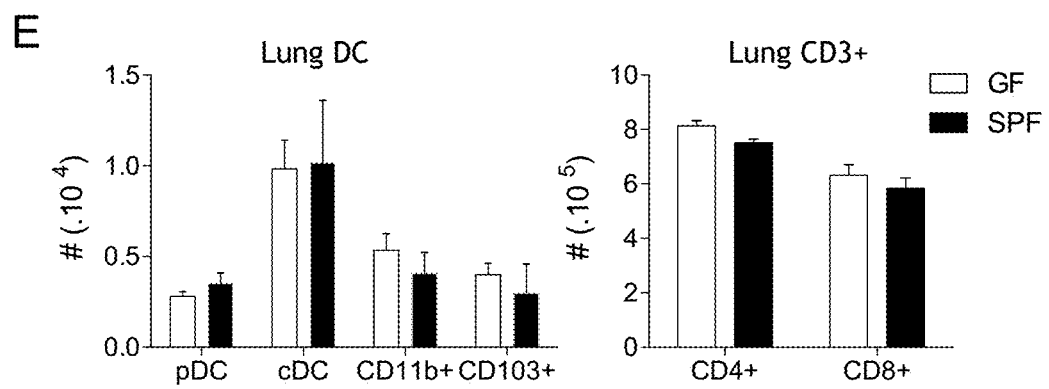

Google English machine translation of RU2575562 accessed Mar. 30, 2020. (Year: 2015).*
Robin Patel et al., Determination of 16S rRNA Sequences of Enterococci and Application to Species Identification of Nonmotile Enterococcus gallinarum Isolates, 1998, Journal of Clinical Microbiology, vol. 36, No. 11, p. 3399-3407 (Year: 1998).*
Amrita Saha, Subhas Chandra Santra, Isolation and characterization of bacteria isolated from municipal solid waste for production of industrial enzymes and waste degradation, 2014, J. Microbiol. Exp., 2014, vol. 1, Issue 1, pp. 12-19 (Year: 2014).*
Atamas, Sergei P. et al., "Cytokines in chronic respiratory diseases" F1000 Reports, 2013, pp. 1-12, vol. 5, No. 3.
Deschemin, Jean-Christophe et al., "The microbiota shifts the iron sensing of intestinal cells" The FASEB Journal, Jan. 2016, pp. 252-261, vol. 30.
Dickson, Robert P. et al., "The Lung Microbiome: New Principles for Respiratory Bacteriology in Health and Disease" PLoS Pathogens, Jul. 2015, pp. 1-5, vol. 11, Issue 7, e1004923.
Erb-Downward, John R. et al., "Analysis of the Lung Microbiome in the "Healthy" Smoker and in COPD" PLoS ONE, Feb. 2011, pp. 1-12, vol. 6, Issue 2, e16384.
Erb-Downward, John R. et al., "The Microbiota in Respiratory Disease" American Journal of Respiratory and Critical Care Medicine, 2012, pp. 1037-1038, vol. 185.
Fontana, Luis et al., "Sources, isolation, characterization and evaluation of probiotics" British Journal of Nutrition, 2013, pp. S35-S50, vol. 109.
Fujimura, Kei E. et al., "House dust exposure mediates gut microbiome Lactobacillus enrichment and airway immune defense against allergens and virus infection" PNAS, Jan. 2014, pp. 805-810, vol. 111, No. 2.
Gollwitzer, Eva S. et al., "Lung microbiota promotes tolerance to allergens in neonates via PD-L1" Nature Medicine, Jun. 2014, pp. 642-647, vol. 20, No. 6.
Hilty, Markus et al., "Disordered Microbial Communities in Asthmatic Airways" PLoS ONE, Jan. 2010, pp. 1-9, vol. 5, Issue 1, e8578.
Jang, Seong-Ok et al., "Asthma Prevention by Lactobacillus Rhamnosus in a Mouse Model is Associated With CD4+CD25+Foxp3+ T Cells" Allergy Asthma Immunol Res., May 2012, pp. 150-156, vol. 4, No. 3.
Kim, H.-J. et al., "Effects of Lactobacillus rhamnosus on asthma with an adoptive transfer of dendritic cells in mice" Journal of Applied Microbiology, 2013, pp. 872-879, vol. 115.
Roux, Xavier et al., "Neonatal lung immune responses show a shift of cytokines and transcription factors toward Th2 and a deficit in conventional and plasmacytoid dendritic cells" Eur. J. Immunol., 2011, pp. 2852-2861, vol. 41.
Sibley, Christopher D. et al., "Culture Enriched Molecular Profiling of the Cystic Fibrosis Airway Microbiome" PLoS ONE, Jul. 2011, pp. 1-11, vol. 6, Issue 7, e22702.
Yun, Yeojun et al., "Environmentally Determined Differences in the Murine Lung Microbiota and Their Relation to Alveolar Architecture" PLoS ONE, Dec. 2014, pp. 1-24, vol. 9, Issue 12, e113466.
Zhang, Bei et al., "Oral administration of Enterococcus faecalis FK-23 suppresses Th17 cell development and attenuates allergic airway responses in mice" International Journal of Molecular Medicine, 2012, pp. 248-254, vol. 30.
International Search Report for PCT/EP2017/051839 dated Apr. 18, 2017.
Flynn, Jeffrey M. et al., "Evidence and Role for Bacterial Mucin Degradation in Cystic Fibrosis Airway Disease" PLOS Pathogens, Aug. 2016, pp. 1-21, vol. 12, No. 8.
Mathieu, Elliot et al., "Paradigms of Lung Microbiota Functions in Health and Disease, Particularly, in Asthma" Frontiers in Physiology, Aug. 2018, pp. 1-11, vol. 9, Article 1168.
Mathieu, Elliot et al., "Oral Primo-Colonizing Bacteria Modulate Inflammation and Gene Expression in Bronchial Epithelial Cells" Microorganisms, 2020, pp. 1-19, vol. 8, No. 1094.
Mehmeti, Ibrahim et al., "Growth Rate-Dependent Control in Enterococcus faecalis: Effects on the Transcriptome and Proteome, and Strong Regulation of Lactate Dehydrogenase" Applied and Environmental Microbiology, Jan. 2012, pp. 170-176, vol. 78, No. 1.
Salze, Marine et al., "Identification of the general stress stimulon related to colonization in Enterococcus faecalis" Archives of Microbiology, 2020, pp. 233-246, vol. 202.
Shimada et al., Effect of Lysed Enterococcus faecalis FK-23 on Allergen-Induced Immune Responses and Intestinal Microflora in Antibiotic-Treated Weaning Mice, J Investing Allergol Clin Immunol 2007; vol. 17 (2): pp. 70-76.
Shimada et al. Effects of Lysed Enterococcus faecalis FK-23 on Allergen-induced Peritoneal Accumulation of Eosinophils and Serum Total IgE Concentration in Inbred Mice, Asian Pacific Journal of Allergy and Immunology 2008; vol. 26: pp. 137-141.

* cited by examiner

D

E

A

B

A

B

C

D

BACTERIAL STRAIN AS AGENTS FOR PREVENTING AND/OR TREATING RESPIRATORY DISORDERS

INTRODUCTION

It was long believed that healthy lungs were sterile and that only the upper airways were colonised by bacteria. However, a pulmonary microbiota was first described in 2010, initially in patients with asthma and chronic obstructive pulmonary disease (COPD), and then in healthy individuals.

The data available in the literature come chiefly from metagenome studies [1,2,3]. Indeed, the bacterial load in healthy lungs is at least an order of magnitude lower than that of the intestine. Most of these strains cannot be detected by conventional technologies based on culture of samples on solid media. However, advances in sequencing technologies have made it possible to identify bacterial strains by sequencing genes encoding 16S rRNA. It was thus shown that the lung microbiota is composed of a relatively large diversity of bacterial species. From a taxonomic point of view, the most widespread phyla identified in the respiratory tract are Proteobacteria, Firmicutes and Bacteroidetes. The most common genera are *Pseudomonas, Streptococcus, Prevotella, Fusobacteria, Veillonella, Haemophilus* and *Neisseria* (Hilty et al., PLoS One. 5(1):e8578, 2010; Erb-Downward et al., PLoS One. 6(2):e16384, 2011).

Colonisation by the microbiota has a very large impact on immunity and health. Research in this area has been facilitated by the use of axenic (germ-free) mice. No resident microorganism of the lung has yet been associated with beneficial effects on pulmonary immunity. Unlike the intestine, for which an abundant bibliography exists, the pulmonary bacterial microbiota remains poorly described, and its influence on the respiratory epithelium and the development of immunity in newborns is an innovative subject.

Respiratory diseases affect the respiratory system and cause disorders of its functioning. According to statistics published in 2012 by the World Health Organisation (WHO), they remain the leading cause of death in children under five worldwide in 2010. Most respiratory infection-causing pathogens are transmitted through the air and/or by direct contact. There is a need in the art to use compositions effectively and easily to treat and prevent respiratory tract infections and their symptoms.

DESCRIPTION

The present invention relates to novel treatments for respiratory diseases, especially asthma. A particular object of the present invention is their prevention.

More particularly, the present inventors have shown that a particular strain of *Enterococcus* sp. has quite advantageous properties in the treatment and/or prevention of respiratory diseases such as asthma.

Indeed, this particular strain limits or even prevents weight loss in an animal model of chronic allergic asthma. In this model, the lungs of animals having received this particular strain show little or no signs of inflammation, which shows the protective effect of said bacterium. The pulmonary epithelium of treated animals has the same thickness as that of healthy animals, while their epithelial cells look very similar to healthy cells. Moreover, the strain of the invention causes increased expression of certain Th1 cytokines but not that of Th2 cytokines, the expression of which may even be decreased in certain cases.

In a first aspect, the invention relates to an *Enterococcus* sp. strain having properties of prevention and/or treatment of respiratory diseases. More specifically, the invention relates to the *Enterococcus* sp. strain deposited under number I-4969 on 14 Apr. 2015 with the Collection nationale des cultures de microorganismes (CNCM), 25 rue du Docteur Roux, 75724 Paris Cedex 15, France.

Strain I-4969 is produced by culture, for example, in a growth medium known to persons skilled in the art (e.g., brain-heart infusion (BHI) medium) for 2 to 3 days, at a temperature of 30-37° C., with or without pH adjustment. The fermentation broth containing the bacterial cells is collected. The broth can be used as is, concentrated, or freeze-dried. Advantageously, the bacteria will be collected, for example by centrifugation, and then resuspended in a suitable buffer, for example PBS (phosphate buffered saline). The bacterial concentration can be established using a flow cytometer or another equivalent process.

The strain of the invention is particularly advantageous in that it causes an increase in the expression of Th1 cytokines but not that of Th2 cytokines, the expression of which may even be decreased in certain cases. It is indeed known to persons skilled in the art that Th2 cytokines are expressed in many respiratory diseases, notably allergic asthma (Atamas et al., F1000 Biol Rep. 2013;5:3). However, it is also known that Th1 cytokines have an inhibitory effect on the Th2 pathway. Without wishing to be bound by the theory, there is evidence that the expression of Th1 cytokines induced by the bacterium of the invention mitigates the effects of respiratory diseases, especially asthma, by less activation of the Th2 response. In fact, the inventors observed that the bacterium of the invention does not activate, or decreases the activation of, the Th2 response and protects against asthma-induced growth retardation.

The terms "Th1 pathway" or "Th1 response", and "Th2 pathway" or "Th2 response", as used herein, refer to the process of differentiation of naive T cells into Th1 or Th2 lymphocytes, respectively. A population of activated CD4 T lymphocytes that direct the immune response towards the cellular response and cytotoxicity are called "Th1 CD4 T lymphocytes". Similarly, "Th2 CD4 T lymphocytes", within the meaning of the invention, correspond to a population of activated CD4 T lymphocytes that direct the immune response towards the humoral response with the production of antibodies and, in the extreme case, synthesis of IgE.

The term "cytokine", as used herein, refers to a family of small secreted regulatory proteins that play a crucial role in immune responses. Cytokines are involved in communication between cells and regulate many cellular functions, such as cell survival and growth, for example, as well as induction of expression of many genes. Cytokines can be produced by many cell types.

The term "Th1 cytokines", as used herein, refers to cytokines produced by Th1 CD4 T lymphocytes (IL-2, IFNγ and TNFβ) or by other cell types in the same context indicating activation of the Th1 pathway (IL-12p70). The term "Th2 cytokines", as used herein, refers to cytokines produced by Th2 CD4 T lymphocytes (IL-4, IL-5, IL-10 and IL-13) or by other cell types in the same context indicating activation of the Th2 pathway (TSLP).

According to the present invention, the terms "overexpression" and "increased expression" refer to an increased expression of a gene of interest, notably a Th1 cytokine gene, relative to that of said gene in a reference control, such as for example a control not treated with the bacterium of the invention. The term "expression", as used herein, refers to the transcription and stable accumulation of sense (mRNA).

Expression also includes translation of mRNA into a polypeptide. The term "increased", as used herein in certain embodiments, means a larger amount, for example, an amount slightly higher than the original amount or, for example, an amount in great excess of the original amount, and notably all quantities in between. Alternatively, "increase" may refer to an amount or an activity that is at least 1%, 2%, 3%, 4%, 5%, 6%, 7%, 8%, 9%, 10%, 11%, 12%, 13%, 14%, 15%, 16%, 17%, 18%, 19% or 20% more than the amount or the activity to which the increased amount or activity is being compared. The terms "raised", "greater than", and "increased" are used interchangeably herein.

The expression "decrease in the Th2 response" or "less activation of the Th2 response", as used herein, refers to a decrease in expression of a gene of interest, notably a Th2 cytokine gene, relative to that of said gene in a reference control, such as for example a control not treated with the bacterium of the invention. The term "decrease", as used herein in certain embodiments, means a smaller amount, for example, an amount slightly smaller than the original amount, or for example an amount much smaller than the original amount, and notably all amounts in between. Alternatively, "decrease" may refer to an amount or an activity that is at least 1%, 2%, 3%, 4%, 5%, 6%, 7%, 8%, 9%, 10%, 11%, 12%, 13%, 14%, 15%, 16%, 17%, 18%, 19% or 20% less than the amount or the activity to which the decreased amount or activity is being compared. The terms "decreased", "smaller than", "less" and "lowered" are used interchangeably herein.

Said "control", as used herein, may be a patient, an animal model, or an in vitro cell model. Preferably, the "control" is a patient. The term "patient", as used herein, refers to a human subject suffering from a respiratory disease, especially asthma.

In another aspect, the present invention also relates to a pharmaceutical composition comprising strain I-4969 and at least one pharmaceutically acceptable excipient.

The inactivated bacterium induces the same effects as the live strain and thus also has properties of prevention and/or treatment of respiratory diseases.

According to a particular embodiment of the invention, the I-4969 strain present in the pharmaceutical composition is an inactivated strain. The expression "inactivated strain", as used herein, refers to a bacterial strain that cannot grow and/or divide. Preferentially, an inactivated strain no longer has metabolic activity. However, the inactivated bacteria of the invention are still able to moderate the Th2 activation pathway, i.e., administration of the inactivated bacterium leads to a decrease in activation of the Th2 pathway.

Bacterial inactivation techniques are well known to persons skilled in the art. Examples include heat inactivation, UV or gamma irradiation, acid treatment, hydrogen peroxide treatment, etc. The bacteria of the invention will be preferentially inactivated by heat treatment.

It is particularly advantageous to use extracts of strain I-4969 in the pharmaceutical compositions of the invention. An "extract", as used herein, refers to any cellular material obtained by lysis of one or several bacterial strains. Advantageously, an extract of the invention has undergone one or several additional extraction and/or purification steps. Preferentially, the extract is obtained from a single strain; more preferentially, said strain is strain I-4969 of the invention.

Lysis can be performed by all means known to persons skilled in the art: alkaline lysis, lysis by sonication, high-pressure lysis (French press), etc. The extract obtained by cell lysis can then be subjected to additional extraction and/or purification steps. These can include any usual treatment of such extracts known to persons skilled in the art: among others, mention may be made of centrifugations (e.g., for separating plasma membrane from cytoplasm), filtrations, precipitations and separations of the various cellular components (e.g., using one of the many types of chromatography), etc. Each of the various extracts obtained in each of these steps can be used in the method of the invention as long as it remains able to moderate the pro-Th2 molecular pathways.

The compositions of the invention are useful for the treatment of respiratory diseases.

The terms "to treat", "treated", "treatment", as well as similar terms, as used herein, refer to the reduction or improvement of symptoms of a disorder (e.g., a respiratory disease, especially asthma) and/or symptoms associated therewith in a subject. It should be noted that, although this is not excluded, the treatment of a disorder or condition does not require that the pathology, condition or symptoms associated therewith are completely eliminated.

The terms "to prevent", "prevention", as well as similar terms, as used herein, refer to suppression of the risk of developing a disorder (e.g., a respiratory disease, especially asthma) and/or symptoms associated therewith in a subject.

The term "subject", as used herein, refers to any mammal that may benefit from the treatment described herein, including humans, dogs, cats, cattle, goats, pigs, sheep and non-human primates. More specifically, a human subject is referred to herein as a "patient". Said patient may belong to any age group, i.e., the patient may be a child, an adolescent or an adult. It is known that children are more susceptible to respiratory diseases, especially asthma. In a preferred embodiment, the patient according to the invention is a child.

The term "respiratory disease", within the meaning of the invention, refers to diseases of the respiratory system or diseases causing respiratory disorders.

More particularly, the compositions of the invention are useful for the treatment and/or prevention of inflammatory respiratory disorders, for example asthma (mild, moderate or severe), for example, bronchial, allergic, intrinsic, extrinsic, exercise-induced, drug-induced (including aspirin and NSAIDs) and dust-induced asthma, steroid-resistant asthma, bronchitis, including infectious and eosinophilic bronchitis, chronic obstructive pulmonary disease (COPD), such as chronic obstructive bronchopneumopathy, cystic fibrosis, pulmonary fibrosis, including cryptogenic fibrosing alveolitis, idiopathic pulmonary fibrosis, interstitial idiopathic pneumonias, fibrosis complicating anti-neoplastic therapy and chronic infection, including tuberculosis and aspergillosis and other fungal infections; complications of lung transplantation; vasculitis and thrombotic disorders of the pulmonary vascular system and pulmonary hypertension (including pulmonary arterial hypertension); antitussive activity including treatment of chronic cough associated with inflammatory and secretory respiratory tract conditions and iatrogenic cough; acute and chronic rhinitis, including drug-induced rhinitis, and vasomotor rhinitis; perennial and seasonal allergic rhinitis including hay fever; nasal polyposis; acute viral infection, including colds, and infection due to respiratory syncytial virus, influenza, coronavirus (especially SARS) and adenovirus, pulmonary oedema, pulmonary embolism, pneumonia, pulmonary sarcoidosis, silicosis, farmer's lung and related diseases; hypersensitivity pneumonitis, respiratory failure, acute respiratory distress syndrome, emphysema, chronic bronchitis, tuberculosis and lung cancer.

In particular, the uses and compositions of the present invention include the prevention and treatment of asthma, COPD and rhinitis. More particularly, the uses and compositions of the present invention relate to the prevention and treatment of asthma. The inventors have shown that strain I-4969, even when heat-inactivated, is particularly effective in preventing asthma when administered before the onset of the disease's symptom set. Therefore, the use of the strain of the invention and the composition comprising same may notably be used effectively to prevent the development of asthma in subjects known to be predisposed to this pathology (e.g., subjects with a familial predisposition to developing asthma).

The term "asthma", as used herein, refers to a chronic inflammatory lung disease characterised by reversible obstruction of the respiratory tract. More particularly, asthma is a chronic inflammatory syndrome of the bronchial mucosa in which many cells play a role (in particular mastocytes, eosinophils and T lymphocytes) in a cascade process. Inflammation causes bronchial smooth muscle contraction (bronchoconstriction) associated with wall swelling. This leads to a reduction in the diameter of the bronchi, hence a limitation of the air flow, which is at least partly reversible (either spontaneously or by therapeutic action). Inflammation also causes an associated increase in airway responsiveness to a variety of stimuli. In addition, inflammation causes hypersecretion of mucus. The disease manifests itself by attacks in the form of wheezing, coughing and shortness of breath (dyspnea).

The pharmaceutical compositions of the invention comprise, in addition to strain I-4969, one or several pharmaceutically acceptable excipients.

The expression "pharmaceutically acceptable excipient", as used herein, refers to an excipient whose administration to an individual is not accompanied by significant deleterious effects. Pharmaceutically acceptable excipients are well known to persons skilled in the art.

As used herein, the expression "pharmaceutically acceptable excipient" includes all solvents, buffers, saline solutions, dispersion media, coatings, antifungal and antibacterial agents, isotonic and absorption-delaying agents, and analogues which are physiologically compatible. The excipients are selected, according to the pharmaceutical form and mode of administration desired, from the usual excipients known to persons skilled in the art. The type of carrier will thus be selected according to the intended route of administration. In various embodiments, the carrier is suitable for intravenous, intraperitoneal, subcutaneous, intramuscular, topical, transdermal or oral administration. Pharmaceutically acceptable vehicles include sterile aqueous solutions or dispersions and sterile powders for extemporaneous preparation of sterile injectable solutions or dispersions. The use of media and agents for pharmaceutically active substances is well known in the art. A typical pharmaceutical composition for intravenous perfusion may be made up to contain 250 mL of sterile Ringer's solution and 100 mg of the combination. Methods for preparing compounds that can be administered via the parenteral route will be known or obvious to persons skilled in the art and are described in greater detail in, for example, Remington's Pharmaceutical Sciences, 17$^{th}$ Ed., Mack Publishing Company, Easton, Pa. (1985), and the 18$^{th}$ and 19$^{th}$ editions of this handbook.

The compositions of the invention are administered to the patient in a therapeutically effective dose. The term "therapeutically effective dose," as used herein, refers to the amount necessary to observe therapeutic or preventive activity on the respiratory disease, especially asthma, particularly the amount needed to observe an improvement in symptoms. The amount of I-4969 bacterium to be administered and the duration of treatment are evaluated by the person skilled in the art based on the physiological state of the subject to be treated, the nature of the arthritic joint(s) to be treated, the selected peptide, and the route of administration used. The bacterial strain used according to the invention can be administered in a single dose or in multiple doses.

The skilled person will thus know how best to choose the routes and modes of administration of the composition of the invention, as well as the optimal dosing regimens and pharmaceutical forms, based on the criteria generally taken into account in the manufacture of a medicinal product or the establishment of a pharmaceutical or veterinary treatment. Preferably, these compounds will be administered systemically, in particular intravenously, intramuscularly, intradermally, intraperitoneally or subcutaneously, orally, or topically (by means of gel, aerosols, drops, etc.). The suitable unit forms of administration include oral forms such as tablets, soft or hard capsules, powders, granules and oral solutions or suspensions; sublingual, buccal, intratracheal, intraocular, intranasal, inhalation forms of administration; topical, transdermal, subcutaneous, intramuscular or intravenous forms of administration; rectal forms of administration; and implants. For topical application, the compounds of the invention can be used in creams, gels, ointments or lotions.

It will be particularly advantageous according to the invention to administer the composition via the enteral, oral, parenteral (e.g., subcutaneous, intradermal, or intramuscular) or mucosal (e.g., intranasal, sublingual, intravaginal, transcutaneous) route. More preferably, the pharmaceutical composition of the invention will be administered on several occasions, spread over time. Its mode of administration, dosing regimen, and optimal pharmaceutical form can be determined according to the criteria generally taken into account in the establishment of a treatment adapted to a patient such as, for example, the age or weight of the patient, the seriousness of his general condition, tolerance to the treatment, and the side effects observed.

In the pharmaceutical compositions of the present invention, the active principle or principles are generally formulated in dosage units. For example, when live I-3699 bacterium is administered, the dosage unit contains between $10^2$ and $10^5$ cfu, advantageously between $10^3$ and $10^5$ cfu, preferably from $10^3$ to $10^4$ cfu per dosage unit, for daily administrations, once or several times per day. Furthermore, when bacterial extracts are administered to the patient, the dosage unit contains 2.5 to 500 mg, advantageously from 10 to 250 mg, preferably from 10 to 150 mg per dosage unit, for daily administrations, one or several times per day. Although these dosages are examples of average situations, there may be particular cases where higher or lower dosages are appropriate; such dosages also belong to the invention. In usual practise, the appropriate dosage for each patient is determined by the doctor according to the mode of administration and to the age, weight and response of said patient.

The invention will be described in greater detail using the examples below.

FIGURE LEGENDS

FIG. 1. The germ-free (GF) lungs are completely functional despite a different homeostasis.

(A) The lungs were fixed, coated with paraffin, and cut into 5-μm sections. The lung sections were stained with haematoxylin eosin saffron (HES) and photographed using a slide scanner and CaseViewer software. A representative section is shown per group.

(B) Ferritin was measured in 30 µg total lung protein. The data are shown individually and as mean±standard deviation.

(C) mRNA level is expressed as 2-ΔCt, calculated from the Ct (cycle threshold) of the mRNA relative to the Ct of the HPRT mRNA (ΔCt). The data are shown individually and as mean±standard deviation.

(D) Western blot of anti-aquaporin-4 and TLR4 from lung proteins.

(E) The lung cells were labelled with a monoclonal antibody (mAb) or an isotypic control and analysed by flow cytometry. The plasmacytoid dendritic cells (pDCs) were identified as $CD11^{c+}$ $MHCII^+$ $mPDCA1^+$ $CD11b^-$ cells. The dendritic cells were analysed by selection of $CD11^{c+}$ cells from CLH $II^{high}$ and analysis of CD11b and CD103 expression, making it possible to define the two main dendritic cell subgroups: $CD11b^+$ $CD103^-$ (CD11b) and $CD11b^-$ $CD103^+$ (CD103). The T cells were identified as $CD3^+$ $CD4^+$ or $CD3^+$ $CD8^+$ cells. The data correspond to the mean±standard deviation of n≥6 mice.

All data were obtained in two independent experiments.

Figure 2:
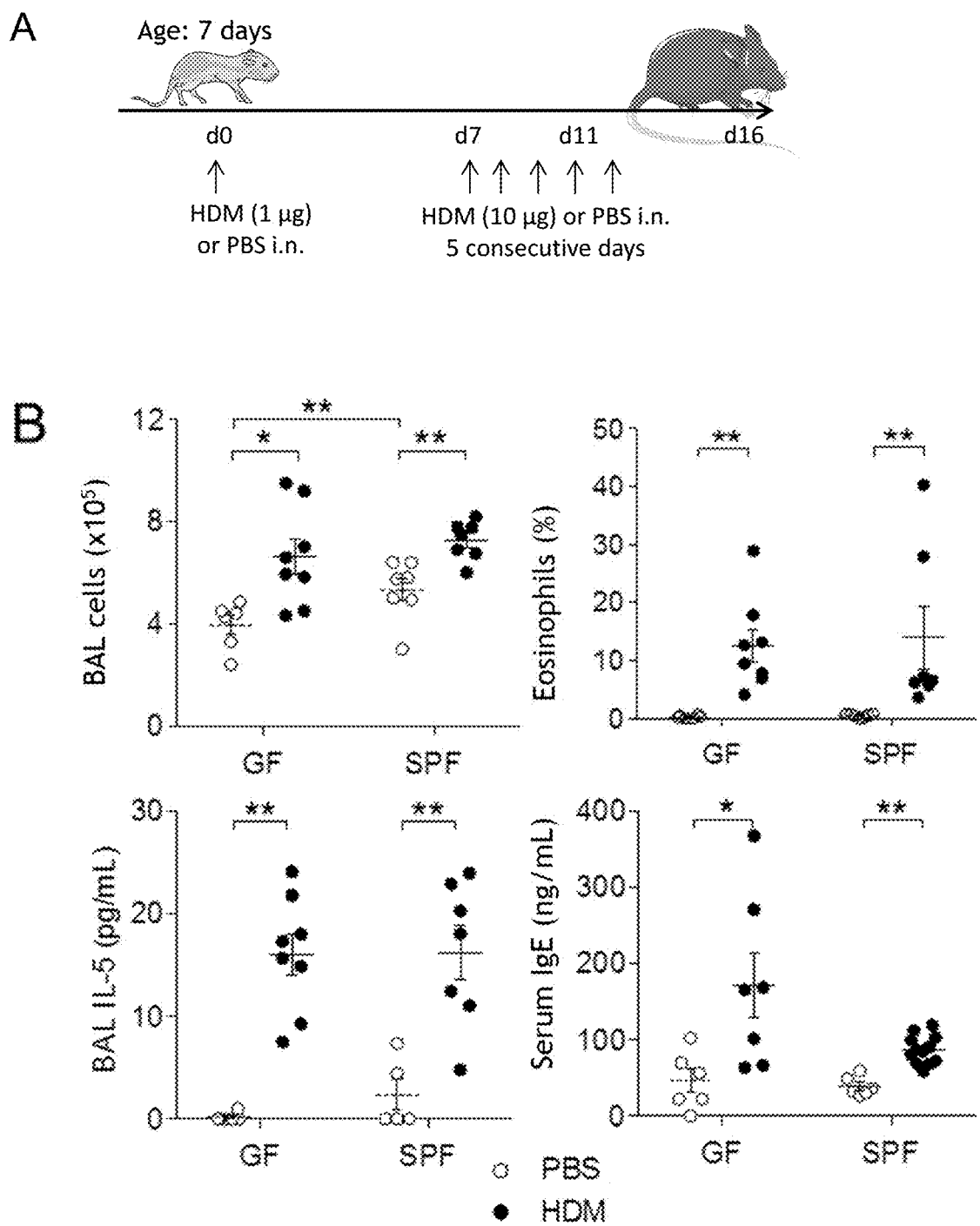
Figure 2:
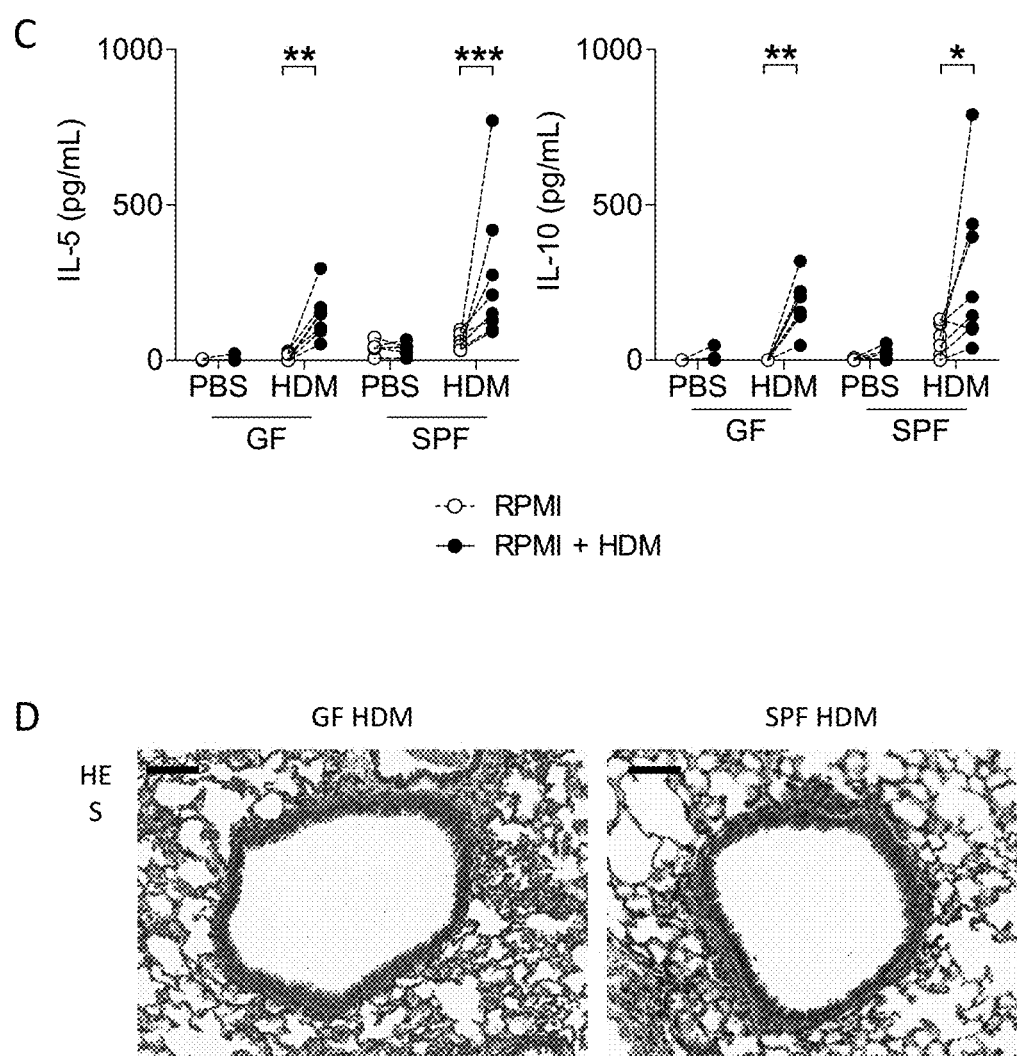

FIG. 2. HDM-induced asthma is not exacerbated in GF mice.

(A) Protocol for inducing asthma with HDM.

(B) The cells present in the bronchoalveolar lavage (BAL) were counted, cytocentrifuged and stained with May-Gründwald-Giemsa. Eosinophils were counted and are expressed as % of total BAL cells. Levels of cytokine IL-5 in the BAL and of serum IgE were measured by ELISA. The data correspond to the mean±standard deviation.

(C) Cells from each respiratory lymph node (RLN) were isolated and cultured 72 hours in RPMI with or without HDM. Supernatant levels of cytokines IL-5 and IL-10 were measured by ELISA. The RPMI±HDM values for the same mouse are connected by a dotted line.

(D) Lung histology was performed as described for FIG. 1. A representative section is shown per group.

Figure 3:
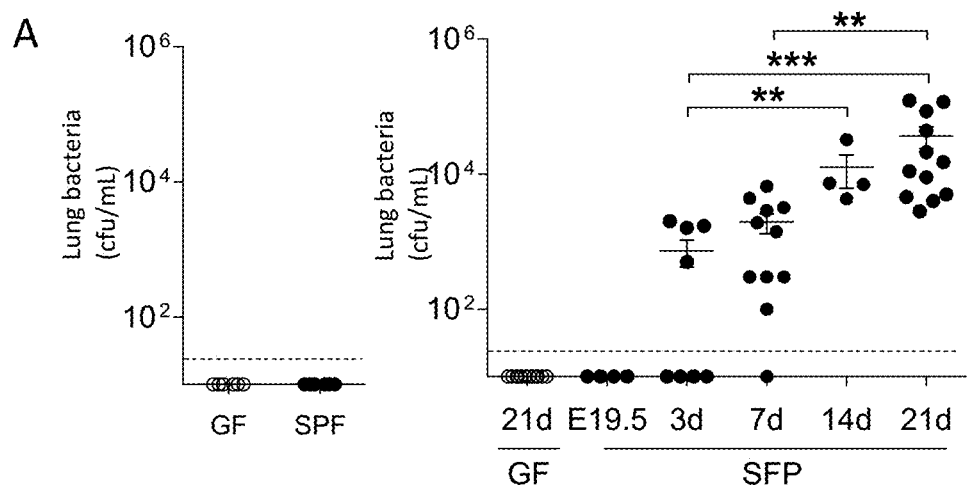
Figure 3:
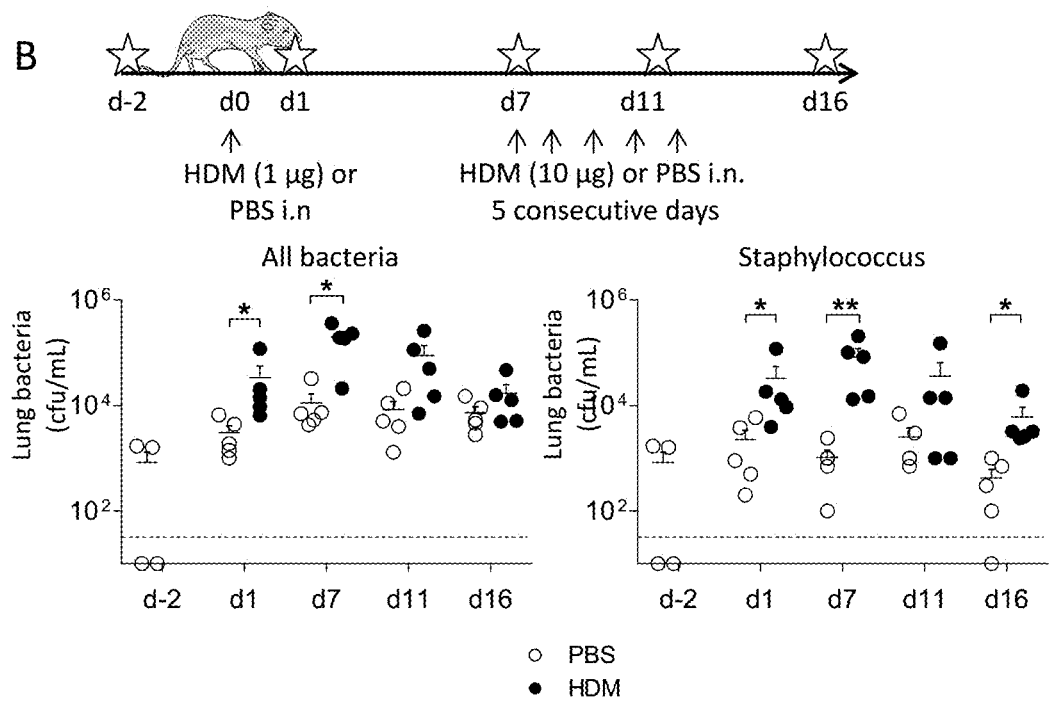
Figure 3:
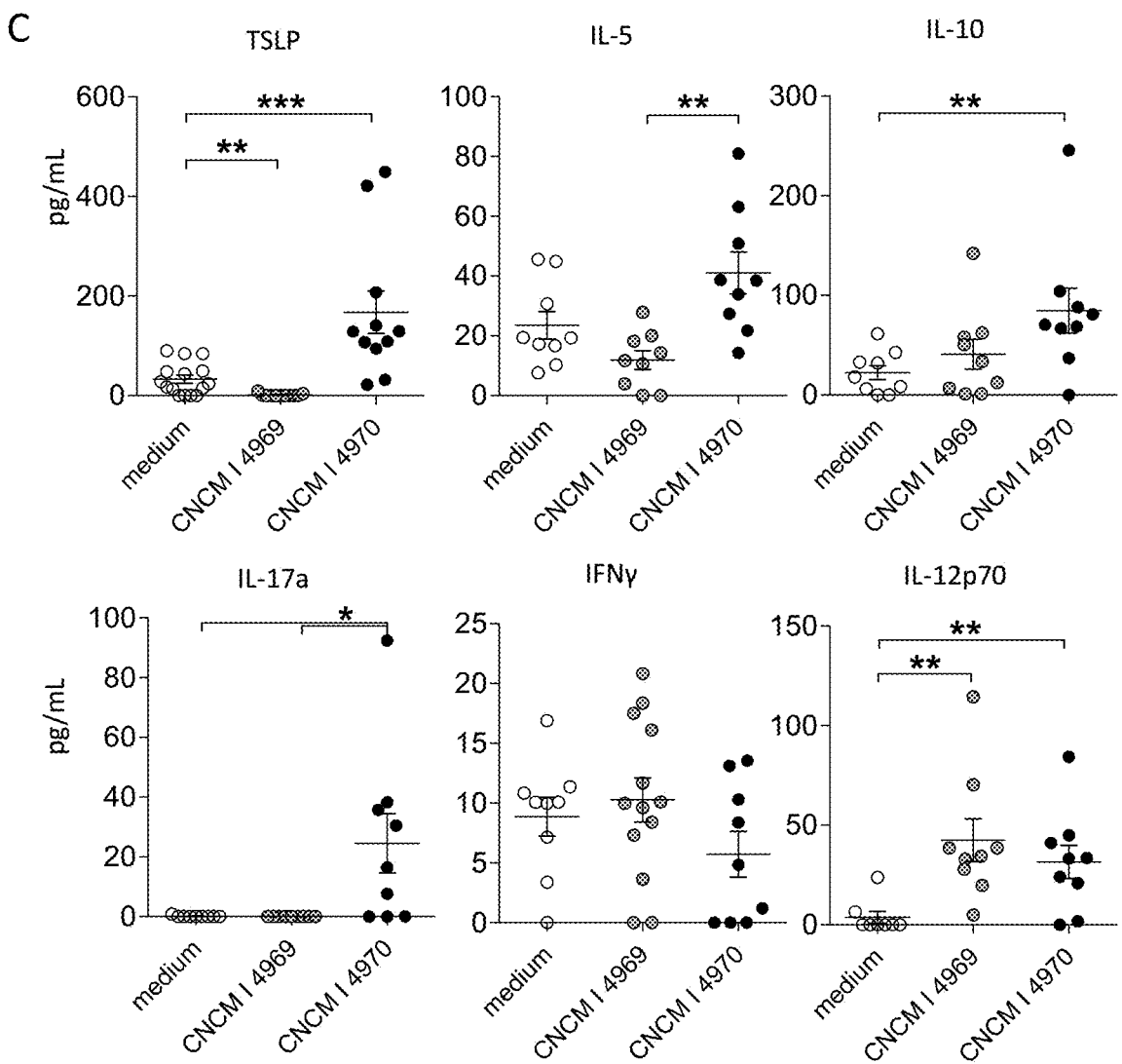

FIG. 3. The lung microbiota is altered during HDM-induced asthma.

(A) BAL or lung homogenates were incubated 24 hours on yhBHI plates and colony forming units (cfu) were counted per mL of BAL or per g of lung.

(B) Experimental design of the protocol and results of the lung bacterial count on different days of the protocol. Lung homogenates were incubated 24 hours on yhBHI plates and total or *Staphylococcus* colony forming units (cfu) were counted per g of lung.

(C) The strains were co-incubated in the presence of lung explants. Cytokines IL-5, IL-10, IL-12p70, IL-17a, IFNγ and TSLP were quantified by ELISA following the manufacturer's instructions. "Medium": bacteria-free culture media control.

Figure 4:
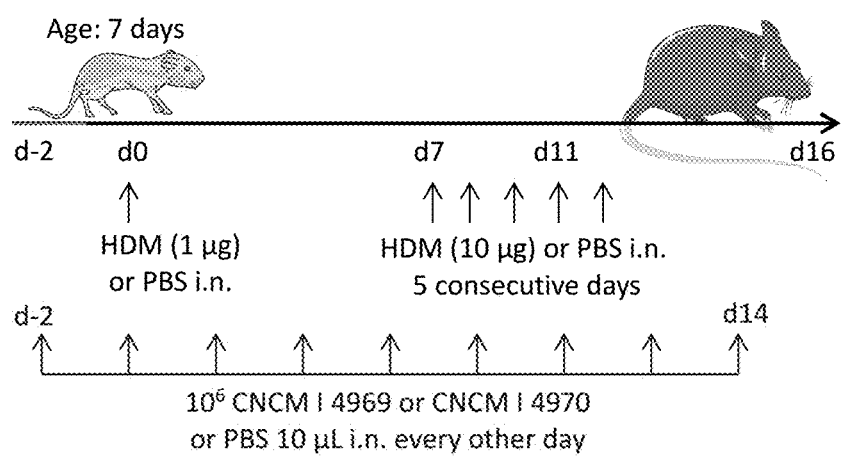
Figure 4:
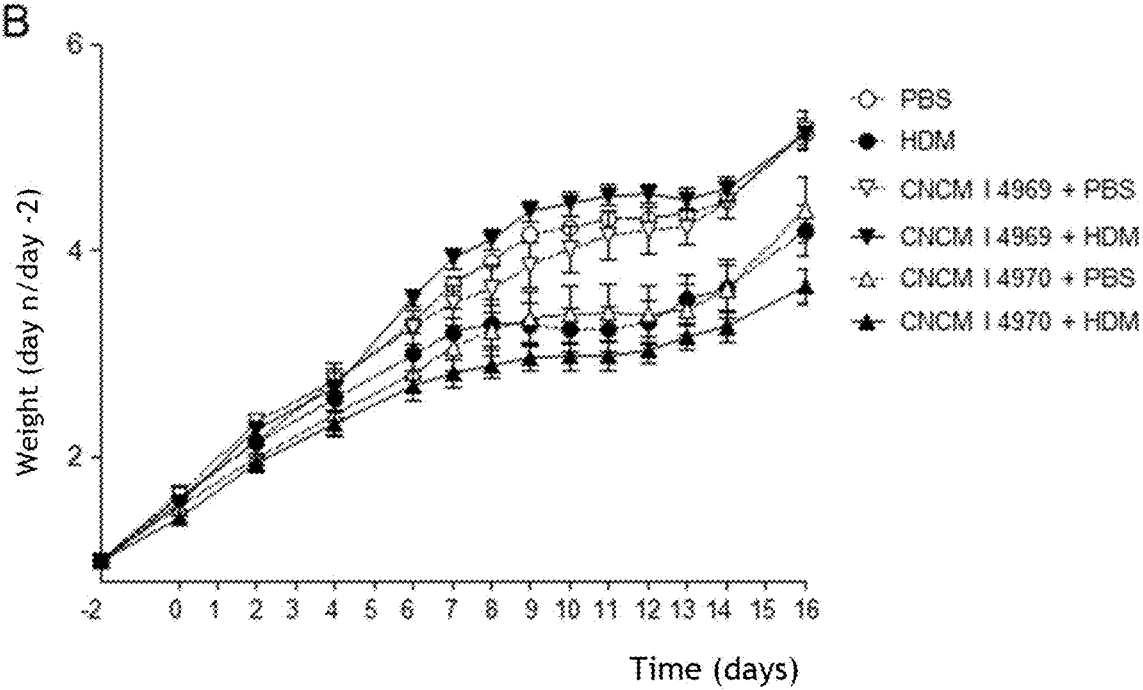

FIG. 4. The bacterial intervention can modulate the features of asthma.

(A) Experimental design of the protocol (B) The mice are weighed daily. The growth curves correspond to the mean±standard deviation of a mouse's weight (normalised to the initial weight at day-2). Tukey's multiple comparison method in the ANOVA was used to compare growth curves.

Figure 5:
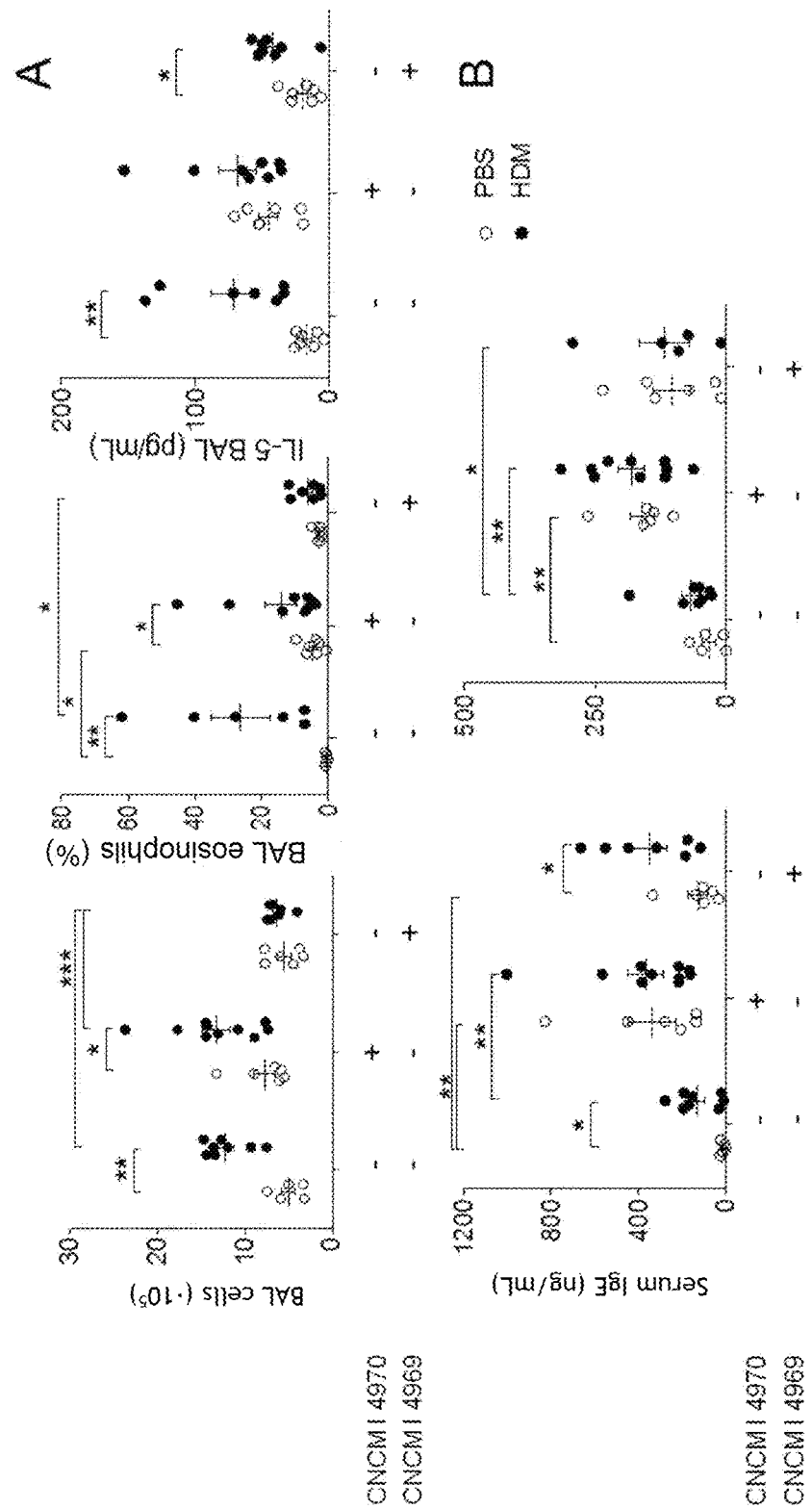
Figure 5:
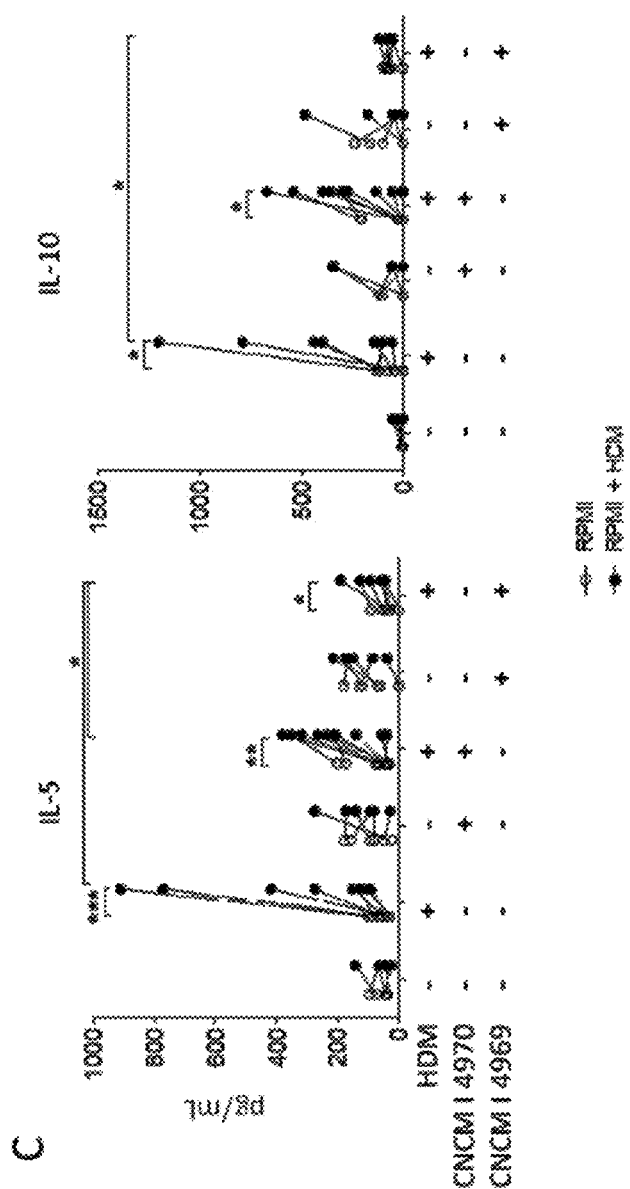

FIG. 5. The Th2 signature is decreased by CNCM I 4969.

(A) The cells present in the bronchoalveolar lavage (BAL) were counted, cytocentrifuged and stained with May-Gründwald-Giemsa. Eosinophils were counted and are expressed as % of total BAL cells. 4969

(B) Levels of cytokine IL-5 in the BAL and of serum IgE were measured by ELISA. The data correspond to the mean±standard deviation.

(C) Cells from each respiratory lymph node (RLN) were isolated and cultured 72 hours in RPMI with or without HDM. Supernatant levels of cytokines IL-5 and IL-10 were measured by ELISA. The RPMI±HDM values for the same mouse are connected by a dotted line.

Figure 6:
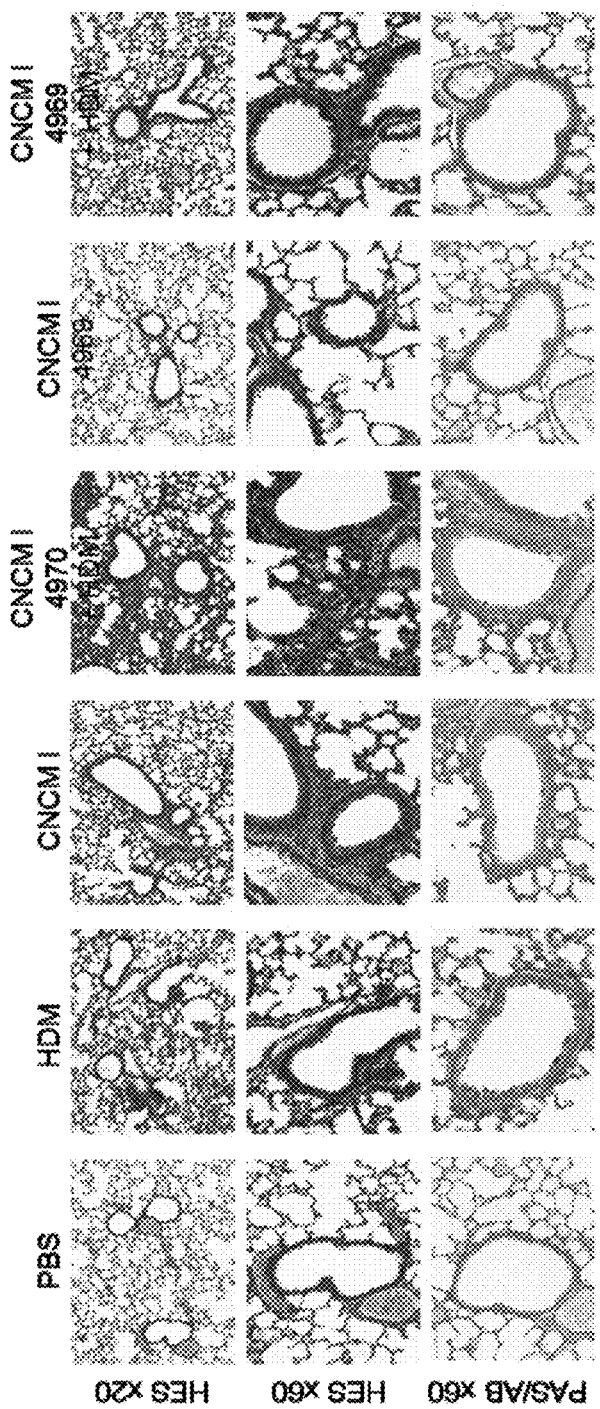
Figure 6:
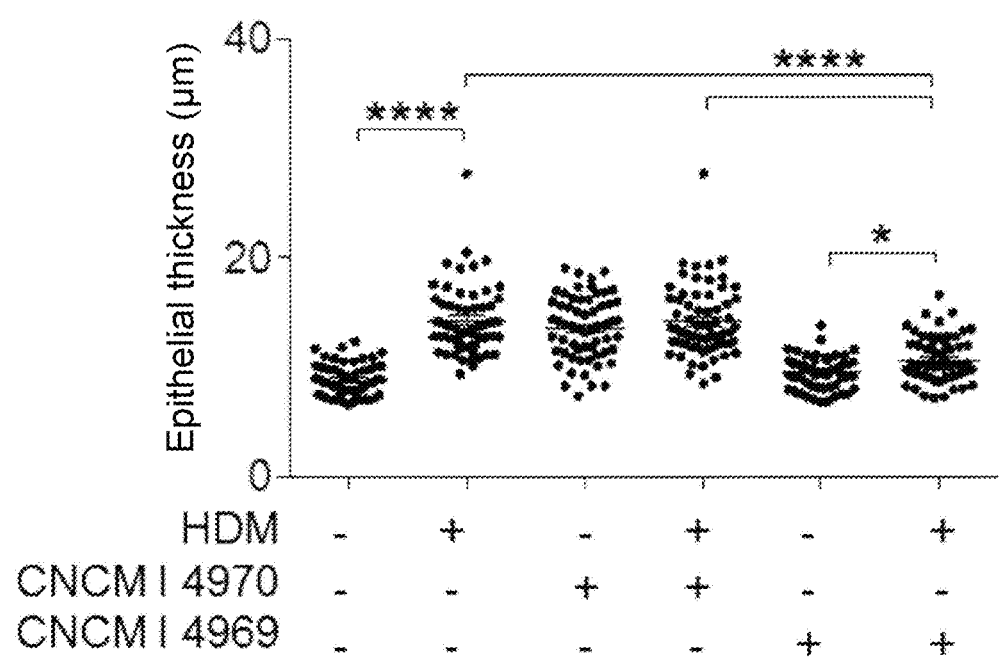

FIG. 6. CNCM I 4969 protects against lung inflammation whereas CNCM I 4970 increases it.

(A) Five-micron lung sections were stained with haematoxylin eosin saffron (HES) or with reactive Alcian blue/periodic acid-Schiff (PAS).

(B) Lung epithelial thickness was measured for each lung section.

Figure 7:
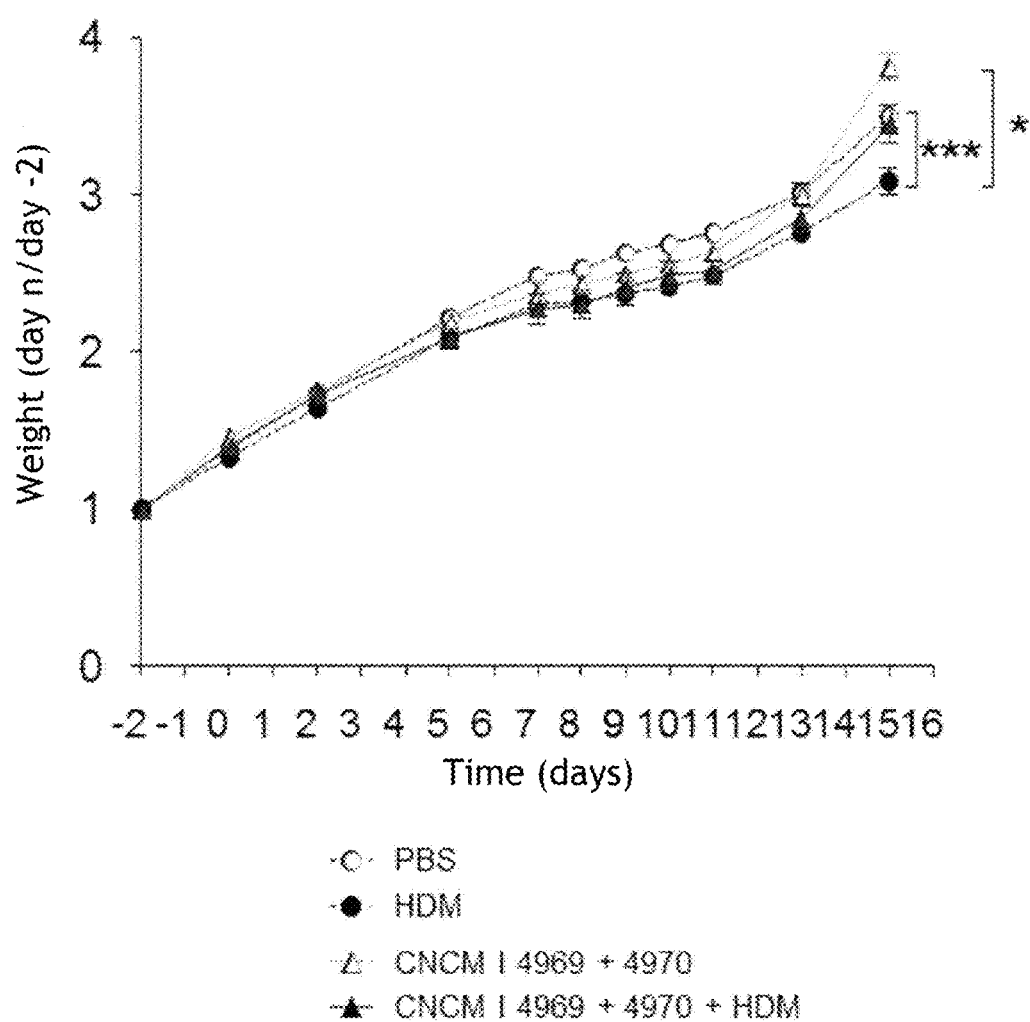
Figure 7:
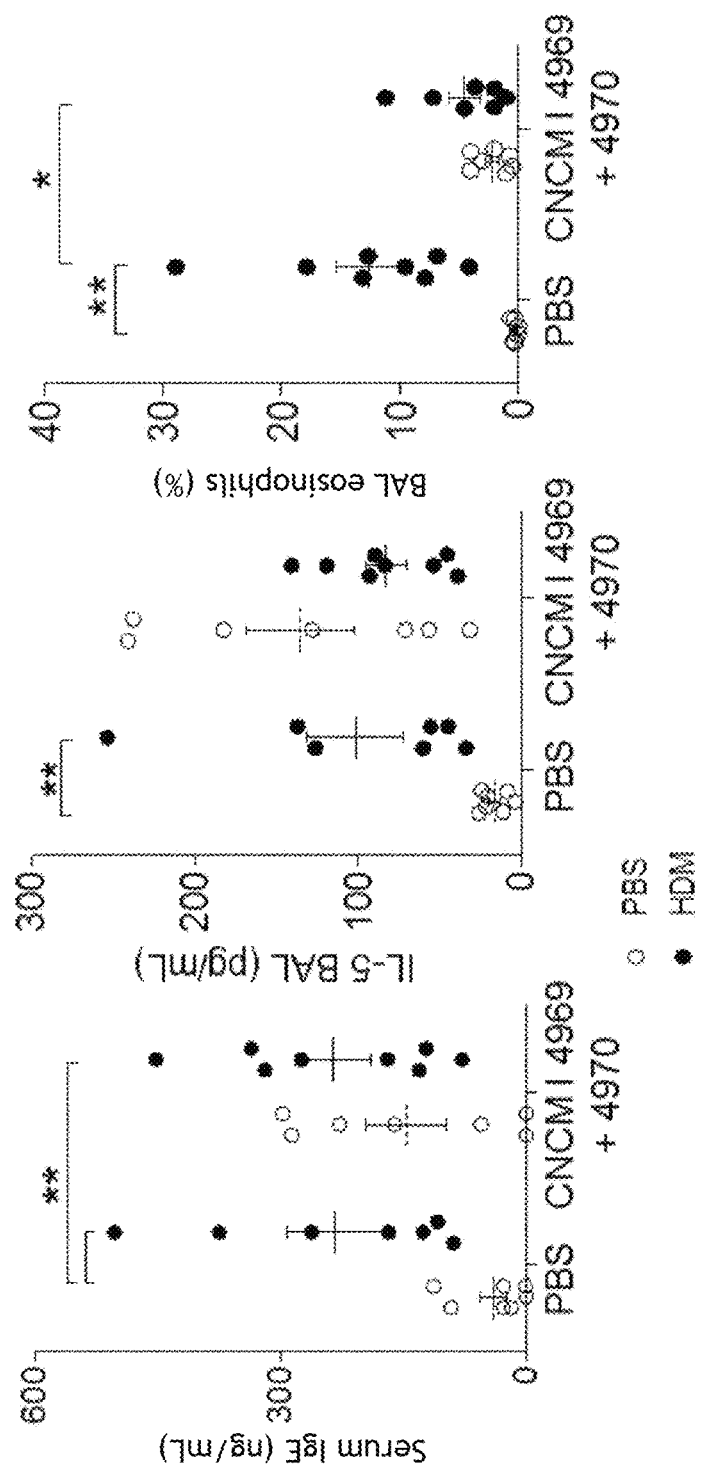
Figure 7:
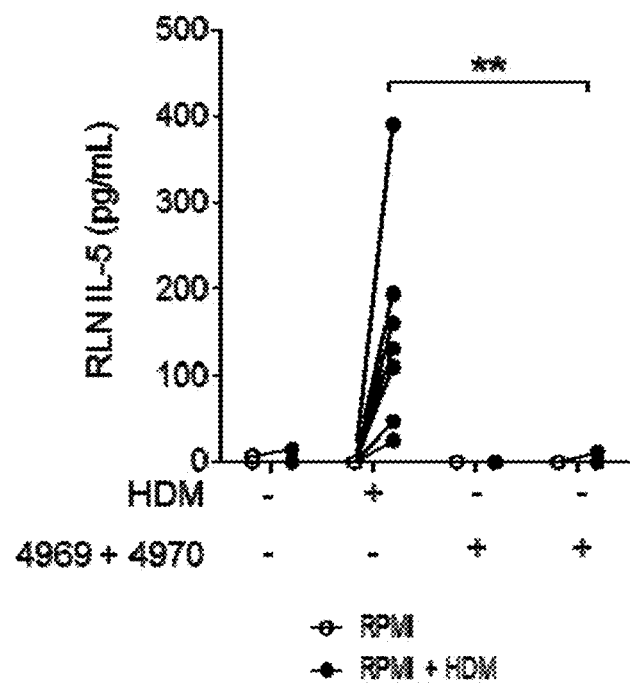
Figure 7:
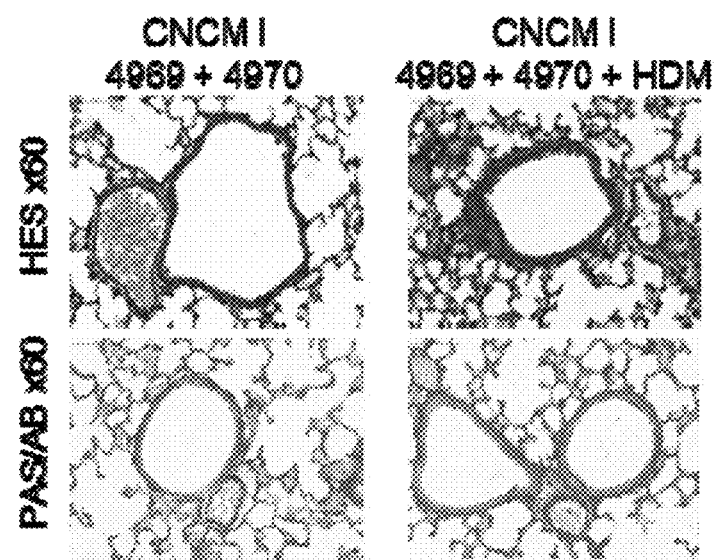

FIG. 7. When administered together, CNCM I 4969 and 4970 induce an intermediate inflammation profile.

(A) The mice are weighed daily. The growth curves correspond to the mean±standard deviation of a mouse's weight (normalised to the initial weight at day-2). Tukey's multiple comparison method in the ANOVA was used to compare growth curves.

(B) The cells present in the bronchoalveolar lavage (BAL) were counted, cytocentrifuged and stained with May-Gründwald-Giemsa. Eosinophils were counted and are expressed as % of total BAL cells.

(C) Cells from each respiratory lymph node (RLN) were isolated and cultured 72 hours in RPMI with or without HDM. Supernatant levels of cytokine IL-5 were measured by ELISA. The RPMI±HDM values for the same mouse are connected by a dotted line.

(D) Five-micron lung sections were stained with haematoxylin eosin saffron (HES) or with reactive Alcian blue/periodic acid-Schiff (PAS).

Figure 8:
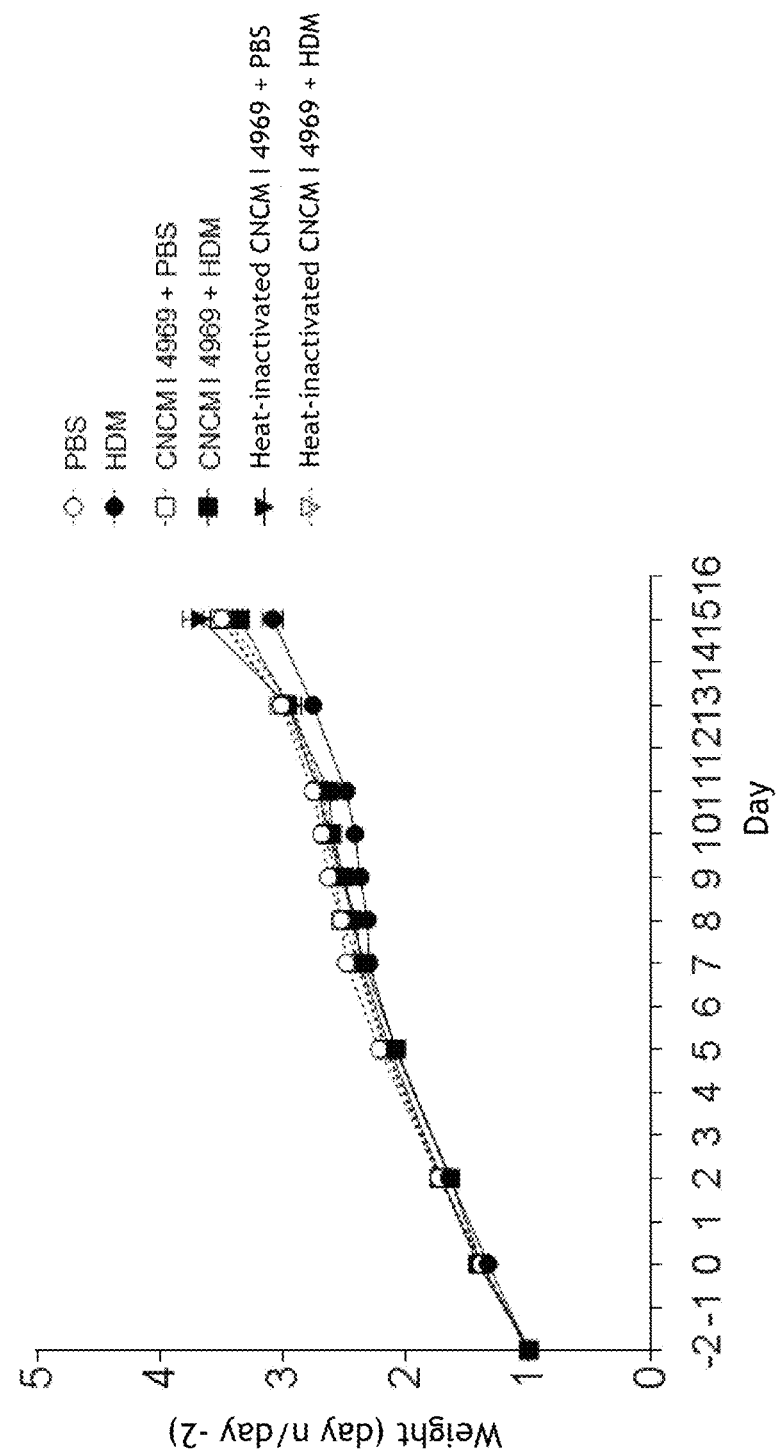

FIG. 8. Heat-inactivated bacterial strain CNCM I 4969 promotes weight gain in asthmatic mice and thus protects them against growth retardation due to asthma.

The mice are weighed daily. The growth curves correspond to the mean±standard deviation of a mouse's weight (normalised to the initial weight at day-2). Tukey's multiple comparison method in the ANOVA was used to compare growth curves.

Figure 9:
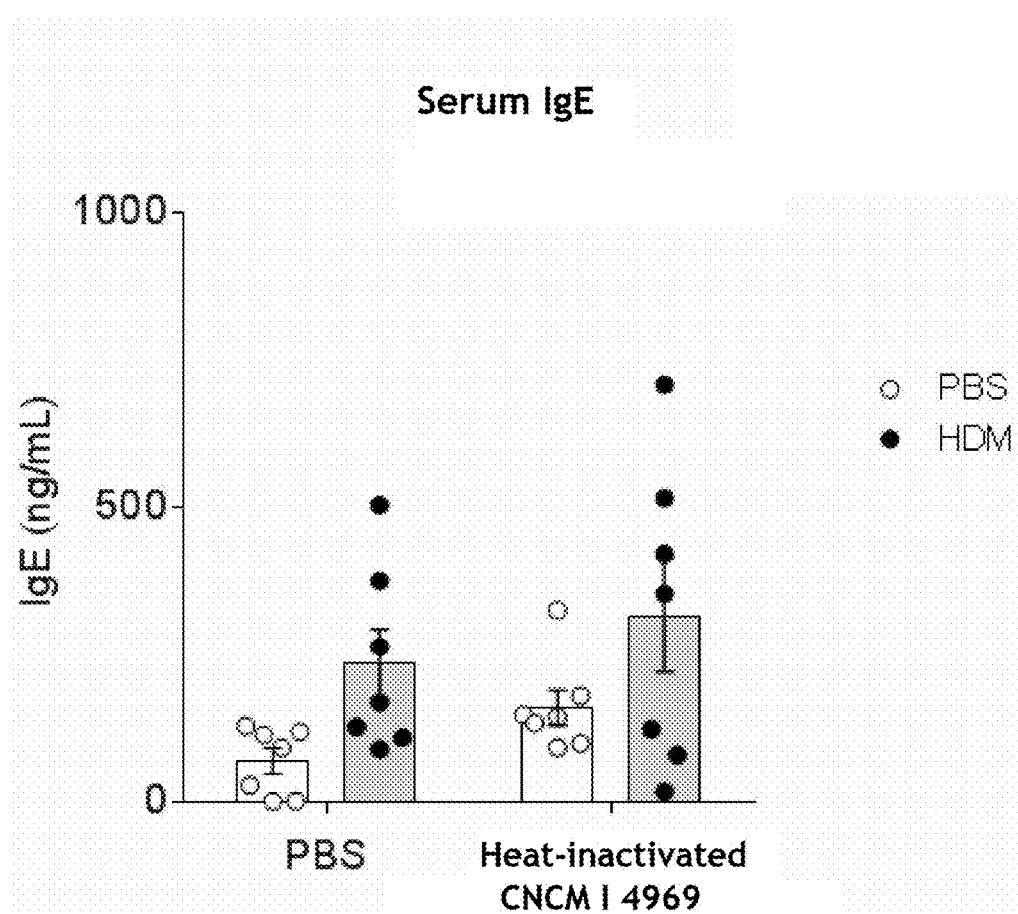

FIG. 9. Heat-inactivated bacterial strain CNCM I 4969 does not induce a decrease in blood IgE.

The serum level of cytokine IgE was measured by ELISA. The data correspond to the mean±standard deviation.

EXAMPLES

1. Experimental Procedures

Effect on Asthma Progression in Mice Inoculated with Bacterial Strain CNCM I 4969

Bacterial Strains, Media, Growth Conditions

Pulmonary bacterial strains were isolated from mouse lung homogenates with a homogeniser (Ultraturax (IKA) or Tissue Lyser (Qiagen)). They were then grown on yhBHI, M17, MRS, or mannitol salt agar medium for 24 to 48 hours at 37° C. under aerobic conditions or 5 days at 37° C. in a Freter chamber under anaerobic conditions. The isolated strains were frozen in 16% glycerol at −80° C. The identity of each strain was confirmed by mass spectrophotometry and PCR sequencing of 16S RNA. The selected strains were deposited with the Collection nationale des cultures de microorganismes (CNCM). The strain of the invention was thus deposited under reference number CNCM I 4969. It should be noted that this strain was originally characterised as a *Streptococcus*. However, subsequent mass spectrophotometry studies have shown that this bacterium belongs to the family *Enterococcus* sp. which is very close to a *Streptococcus*. In addition, a *Staphylococcus sciuri* strain was isolated in the same screen (CNCM I 4970).

Animals and Related Procedures

The present animal experiments were approved by the COMETHEA ethics committee under number 01553.01. SPF The C57BL/6 mice were obtained from Janvier (Le Genest, St Isle, France). They were crossed and raised under FELASA SPF conditions in our animal care facilities (IERP, INRA, Jouy-en-Josas or VIB, Gent). The GF C57BL/6 mice were obtained from CDTA (CNRS, Orleans, France) or by in-house reproduction (INRA, Jouy-en-Josas). They were crossed and raised under sterile conditions in Trexler isolators (Calhène, Vélizy, France) in the Anaxem animal facility (INRA, Jouy-en-Josas). For induction of allergic asthma by HDM, 7-day-old mouse pups received 1 μg of HDM (Greer) or PBS without LPS (Lonza) in a total volume of 10 μL. One week later, they received 10 μg of HDM (or PBS) for 5 consecutive days. In some experiments, 5-day-old mouse pups received $1 \cdot 10^6$ bacteria in PBS in a total volume of 10 μL, every other day.

Sample Collection

The mice were sacrificed by overdose of ketamine and xylazine. Bronchoalveolar lavage (BAL) was performed on the right lobes with PBS 1 mM EDTA as previously described (Roux et al., 2011). BAL supernatants were frozen and stored at −20° C. BAL cells were cytocentrifuged (Cytospin 5) on microscope slides (Superfrost), then stained with May-Gründwald and Giemsa. The right lobe was used for flow cytometry or for counting bacteria on plates of gelled medium after homogenisation with a Tissue Lyser. For flow cytometry, the right lobe and the respiratory lymph nodes (RLN) (cervical, mastoid and mediastinal) were treated with 1 mg/mL collagenase D and 0.5 mg/mL DNase I to isolate the cells. The left lung lobe was kept at −80° C. until use to extract the RNA. Alternatively, the lungs were fixed with 4% paraformaldehyde (PFA) and coated with paraffin before histological examination.

Histology

Five-micron lung sections were stained with haematoxylin eosin saffron (HES) or with reactive Alcian blue/periodic acid-Schiff (PAS) and photographed using the CaseViewer software program.

Analysis of Gene Expression by q-RT-PCR

Total RNA was extracted from lung homogenates using the NucleoSpin® RNA Kit (Macherey Nagel). cDNAs were obtained by reverse-transcription using random primers and reverse transcriptase (High-Capacity cDNA Archive Kit, Applied Biosystem by Life Technologies SAS, Saint Aubin, France) according to the manufacturer's instructions. The primers used (Sigma-Aldrich, Eurogentec) are listed in Supplementary Table 1. The q-RT-PCR reaction was repeated three times for each gene using the AbiPrism 7000 system (Applied Biosystem) and Takyon™ ROx SYBR MasterMix (Eurogentec). The data were analysed with the 7000 System SDS program (Applied Biosystem) to determine the cycle threshold (Ct) values. Messenger RNA (mRNA) expression was calculated with the ΔCt method and related to mHPRT expression.

Western Blot

Protein extractions and immunoblotting experiments were performed as previously described (Deschemin et al., 2015). The antibodies used are as follows: anti-mouse TLR4 (sc-30002, Santa Cruz); anti-aquaporin-4 (sc-20812, Santa Cruz) and anti-β-actin (Sigma AC-74, product number A5316). The secondary antibodies used were anti-goat (Calbiochem) or anti-rabbit (Jackson ImmunoResearch Laboratories) antibodies.

Flow Cytometry

After being saturated with anti-CD32/CD16 antibodies, the cells were incubated with monoclonal antibodies (mAb) directed against mPDCA1 (JF05-1C2.4.1, FITC-conjugated), MHCII (IA/IE, 2G9 or M5/114.15.2, FITC or EP), CD103 (M290 or 145-2D11, PE), CD86 (GL1, FITC) CD11b (M1/70, PerCP Cy5.5) or CD11c (HL3, Biotin or BV786). For T-cell labelling, the cells were incubated with antibodies directed against CD4 (L3T4 or RM4-5, FITC or PECy7), CD45.2 (104, A780), CD3 (145-2C11, PerCP Cy5.5) and CD8 (Ly2, 53-6.8, Biotin or APC). All mAb were obtained from BD Biosciences except for mPDCA1 (Miltenyi Biotec). APC-conjugated streptavidin (BD Biosciences) was used to label the antibody-biotin. At least $2 \cdot 10^6$ events were acquired with an Accuri or Fortessa FACS (BD Biosciences) which were then analysed with the FlowJo Software v7.5 program (Tree Star Inc).

ELISA of Cytokines and Ig

Cytokines IL-5, IL-10, IL-12p70, IL-17a and IFNγ (Mabtech) TSLP (Ready-SET-Go, eBioscience) were quantified by ELISA following the manufacturer's instructions. IgE and IgG1 were measured in serum from different mice (Ready-SET-Go, eBioscience) following the manufacturer's instructions.

Statistical Analysis

The nonparametric Mann-Whitney test (comparison of 2 groups, n≥4), or Tukey's multiple comparison method (>2 groups) was used to compare the unpaired values (GraphPadPrism software). Significance is represented: * $p<0.05$;  $p<0.01$; * $p<0.001$; and **** $p<0.0001$.

Effect on Asthma Progression in Mice Inoculated with Heat-Inactivated Bacterial Strain CNCM I 4969

CNCM69 cultures were obtained as previously described ($10^8$ cfu/mL) then optionally incubated for 10 min at 100° C. in a water bath. After this treatment, the culture was spread over yhBHI agar medium for 24 hours at 37° C. to verify the effectiveness of the heat treatment. No bacteria grew after the heat treatment, whereas cultures grew (after 24 hours at 37° C.) for the tubes not having undergone heat shock.

The protocol for administering the strain and triggering asthma in the presence of HDM is as described in FIG. 2A of the present application. The same animal inoculation procedure as described above was used but the inoculated CNCM69 strain was optionally inactivated by heat treatment.

In addition, serum IgE level was measured by ELISA in two groups of HDM mice inoculated with strain CNCM69 optionally inactivated by heat treatment. The assay protocol is the same as previously described in the legend for FIG. 5B.

2. Results

In order to isolate lung-resident bacteria capable of modulating host susceptibility to respiratory diseases, a model of induced asthma in mouse pups was used. It was first shown that the lungs of germ-free (GF) mice are functional despite a different homeostasis (FIG. 1). When allergic asthma is induced, it is not exacerbated in GF mice relative to the control (FIG. 2).

After the induction of allergic asthma in mouse pups, the lung microbiota is altered. Indeed, the number of bacteria cultured per gram of lung increases significantly when pulmonary inflammation begins (FIG. 3A). Certain bacteria in particular participate in this increase, whereas other bacteria do not vary significantly between treated animals and controls (FIG. 3B). This result demonstrates that a respiratory pathology such as asthma is associated with a change in lung-resident bacterial populations.

Early-colonising bacteria of mouse pup lungs were isolated very early after birth (3 days) and until weaning (3 weeks). These bacteria are alive, and can be cultured in the absence or presence of oxygen.

One strain was deposited with the CNCM under number CNCM I-4969. This bacterium has immunomodulatory properties. When these early-colonising bacteria are co-cultured on lung sections, they induce a strong and specific tissue response, since the immune responses measured by ELISA are different depending the bacterium used (FIG. 3C). For example, the secretion of Th1 (IFNγ, IL-12p70), Th2 (TSLP) and anti-inflammatory cytokines (IL-10) was measured in the presence of various bacteria, including CNCM I-4969 and other respiratory bacteria isolated in the laboratory (an *E. coli* strain and a *Proteus mirabilis*).

Our results show that bacterium CNCM 64969, which is an early-colonising bacterium of the lung, has immunomodulatory properties (table below).

| Strains | Ex vivo functional screening (PCLS, FIG. 3) | In vivo progression during asthma (FIG. 1) | |
|---|---|---|---|
| A | N/A | Th1 | No variation |
| B | N/A | Th1 | No variation |
| CNCM I 4969 | *Streptococcus* | Th1 | No variation |
| CNCM I 4970 | N/A | Th2 | increases |

This aspect was studied in greater detail by testing strain I-4969 in vivo in mice as described below.

Our results show that mouse pups receiving bacterium CNCM 4969 are protected against growth retardation due to asthma (FIG. 4).

The table below and FIG. 8 show that this protection against growth retardation in mouse pups is also maintained after inoculation of heat-deactivated strain CNCM 4969.

We then analysed several immune and inflammatory parameters. We observed that bacterium CNCM 4970 increases the amount of IgE in the blood (this type of immunoglobulin is increased during allergic reactions) (FIG. 5B). By restimulating the respiratory ganglia cells in vitro with medium alone or medium containing HDM, we noted that Th2 cytokines are significantly less increased for those receiving CNCM 4969 (FIG. 5C). On the other hand, lung inflammation is reduced in the presence of CNCM I-4969, as various physiological parameters show (FIG. 6). In contrast, strain CNCM I-4970 exacerbates this inflammation. We conclude that bacterium CNCM 4969 reduces the Th2 signature, and protects against growth retardation, which gives it protective properties against asthma.

In addition, the results obtained after the assay of blood IgE level in mice inoculated with heat-inactivated strain CNCM 4969 show that this level does not decrease, suggesting that the Th2 signature is not increased (FIG. 9).

With regard to heat-inactivated CNCM 4969 bacteria, we can also conclude that they confer protective properties against asthma.

The second experiment we carried out confirms the weight curves of the first. For this $2^{nd}$ experiment, we had more mouse pups and were able to add the groups: the two bacteria together (FIG. 7); heat-inactivated bacteria. Our results, based on weight curves and blood IgE assays, show that the two bacteria administered together induce an intermediate profile relative to the results observed with CNCM 4969 or 70 alone.

REFERENCES

1. Sibley C D, Grinwis M E, Field T R, Eshaghurshan C S, Faria M M, et al. (2011) Culture Enriched Molecular Profiling of the Cystic Fibrosis Airway Microbiome. PLoSONE 6: e22702.
2. Gollwitzer E, Saglani S, Trompette A, Yadava K, Sherburn R, et al. (2014) Lung microbiota promotes tolerance to allergens in neonates via PD-L1. Nature medicine 20: 642-647.
3. Erb-Downward J R, Thompson D L, Han M K, Freeman C M, McCloskey L, et al. (2011) Analysis of the Lung Microbiome in the "Healthy" Smoker and in COPD. PloSONE 6.

| Tukey's multiple comparison method | Mean difference | q | Significant? p < 0.05? | Summary | 95% CI of the diff. |
|---|---|---|---|---|---|
| PBS vs HDM | 0.1584 | 8.100 | Yes | *** | 0.07633 to 0.2406 |
| PBS vs CNCM I 4969 + PBS | 0.01299 | 0.6639 | No | ns | −0.06912 to 0.09510 |
| PBS vs CNCM I 4969 + HDM | 0.07679 | 3.925 | No | ns | −0.005323 to 0.1589 |
| PBS vs heat-inactivated CNCM I 4969 + PBS | 0.02078 | 1.062 | No | ns | −0.06133 to 0.1029 |
| PBS vs heat-inactivated CNCM I 4969 + HDM | −0.01388 | 0.8631 | No | ns | −0.09899 to 0.06523 |
| HDM vs CNCM I 4969 + PBS | −0.1455 | 7.436 | Yes | *** | −0.2276 to −0.06335 |
| HDM vs CNCM I 4969 + HDM | −0.08166 | 4.174 | No | ns | −0.1638 to 0.0004534 |
| HDM vs heat-inactivated CNCM I 4969 + PBS | −0.1377 | 7.037 | Yes | *** | −0.2198 to −0.05555 |
| HDM vs heat-inactivated CNCM I 4969 + HDM | −0.1753 | 8.963 | Yes | *** | −0.2574 to −0.09322 |
| CNCM I 4969 + PBS vs CNCM I 4969 + HDM | 0.0638 | 3.261 | No | ns | −0.01831 to 0.1459 |
| CNCM I 4969 + PBS vs heat-inactivated CNCM I 4969 + PBS | 0.007792 | 0.3984 | No | ns | −0.07432 to 0.08990 |
| CNCM I 4969 + PBS vs heat-inactivated CNCM I 4969 + HDM | −0.02987 | 1.527 | No | ns | −0.1120 to 0.05224 |
| CNCM I 4969 + HDM vs heat-inactivated CNCM I 4969 + PBS | −0.05601 | 2.863 | No | ns | −0.1382 to 0.02610 |
| CNCM I 4969 + HDM vs heat-inactivated CNCM I 4969 + HDM | −0.09367 | 4.788 | Yes | * | −0.1758 to −0.01156 |
| Heat-inactivated CNCM I 4969 + PBS vs heat-inactivated CNCM I 4969 + HDM | −0.03766 | 1.925 | No | ns | −0.1198 to 0.04445 |

4. Erb-Downward J R, Huffnagle G B, and Martinez F J (2012) The Microbiota in Respiratory Disease. American Journal of Respiratory and Critical Care Medicine 185: 1037-1038.

5. Yun Y, Srinivas G, Kuenzel S, Linnenbrink M, Alnahas S, et al. (2014) Environmentally determined differences in the murine lung microbiota and their relation to alveolar architecture. PLoS One 9: e1134.

6. Jang S, Kim H, Kim Y, Kang M, Kwon J, et al. (2012) Asthma Prevention by *Lactobacillus Rhamnosus* in a Mouse Model is Associated With CD4(+)CD25(+)Foxp3(+) T Cells. Allergy, asthma & immunol research 4: 150-156.

7. Kim H, Kim Y, Lee S, Kang M, Yu H, et al. (2013) Effects of *Lactobacillus rhamnosus* on asthma with an adoptive transfer of dendritic cells in mice. Journal of applied microbiology 115: 872-879.

The invention claimed is:

1. A freeze-dried composition comprising an *Enterococcus* sp. strain deposited with the Collection nationale des cultures de microorganismes (CNCM, 25 rue du Docteur Roux, 75724 Paris Cedex 15, France) under number 1-4969.

2. The composition of claim 1, wherein the strain is inactivated.

3. The composition of claim 2, wherein the strain is heat-inactivated.

4. The composition of claim 2, wherein the strain is present in the form of an extract.

5. A composition comprising an *Enterococcus* sp. strain deposited with the Collection nationale des cultures de microorganismes (CNCM, 25 rue du Docteur Roux, 75724 Paris Cedex 15, France) under number 1-4969 and at least one antifungal or antibacterial agent.

6. The composition of claim 5, wherein the strain is inactivated.

7. The composition of claim 6, wherein the strain is heat-inactivated.

8. The composition of claim 6, wherein the strain is present in the form of an extract.

9. A method for the treatment and/or reduction of the development of one or more respiratory diseases comprising administering a pharmaceutical composition comprising an *Enterococcus* sp. strain deposited with the Collection nationale des cultures de microorganismes (CNCM, 25 rue du Docteur Roux, 75724 Paris Cedex 15, France) under number 1-4969 and at least one pharmaceutically acceptable excipient to a patient in need therefor.

10. The method according to claim 9, wherein the expression of TH2 cytokines is not increased or is decreased in a patient treated with said strain relative to a patient not treated with said strain.

11. The method of claim 9, wherein the treated patient is a child.

12. The method of claim 9, wherein the strain comprised in the composition is inactivated.

13. The method of claim 12, wherein the strain comprised in the composition is heat inactivated.

14. The method of claim 12, wherein the strain is present in the form of an extract.

15. The method of claim 10, wherein the strain comprised in the composition is inactivated.

16. The method of claim 15, wherein the strain comprised in the composition is heat inactivated.

17. The method of claim 16, wherein the strain is present in the form of an extract.

18. The method according to claim 10, wherein the treated patient is a child.

19. The method according to claim 12, wherein the treated patient is a child.

20. The method according to claim 13, wherein the treated patient is a child.

21. The method according to claim 14, wherein the treated patient is a child.

22. The method of claim 9, wherein said respiratory disease is selected from asthma; bronchitis; infectious bronchitis; eosinophilic bronchitis; chronic obstructive pulmonary disease (COPD); chronic obstructive bronchopneumopathy; cystic fibrosis; pulmonary fibrosis; cryptogenic fibrosing alveolitis; idiopathic pulmonary fibrosis; interstitial idiopathic pneumonias; fibrosis complicating anti-neoplastic therapy; chronic infection; tuberculosis; aspergillosis; fungal infection; complications of lung transplantation; vasculitis; thrombotic disorders of the pulmonary vascular system; pulmonary hypertension; pulmonary arterial hypertension; chronic cough associated with inflammatory and secretory respiratory tract conditions; iatrogenic cough; acute rhinitis; chronic rhinitis; drug-induced rhinitis; vasomotor rhinitis; perennial allergic rhinitis; seasonal allergic rhinitis; hay fever; nasal polyposis; acute viral infection; cold common colds; infection due to respiratory syncytial virus, influenza, coronavirus, severe acute respiratory syndrome (SARS) or adenovirus; pulmonary oedema; pulmonary embolism; pneumonia; pulmonary sarcoidosis; silicosis; farmer's lung; hypersensitivity pneumonitis; respiratory failure; acute respiratory distress syndrome; emphysema; chronic bronchitis; tuberculosis or lung cancer.

23. The method of claim 22, wherein said asthma is selected from bronchial asthma, allergic asthma, intrinsic asthma, extrinsic asthma, exercise-induced asthma, drug-induced asthma, dust-induced asthma, or steroid-resistant asthma.

* * * * *